(12) United States Patent
Riefler et al.

(10) Patent No.: US 11,819,557 B2
(45) Date of Patent: Nov. 21, 2023

(54) METHOD FOR PREPARING STABLE LIQUID EMULSION FORMS OF PLANT EXTRACT

(71) Applicant: Sorse Technology Corporation, Seattle, WA (US)

(72) Inventors: Rodger Scott Riefler, Monroe, WA (US); Juan Jorge Ayala, Redmond, WA (US); Howard M. Lee, Seattle, WA (US)

(73) Assignee: Sorse Technology Corporation, Seattle, WA (US)

( * ) Notice: Subject to any disclaimer, the term of this patent is extended or adjusted under 35 U.S.C. 154(b) by 0 days.

(21) Appl. No.: 17/566,549

(22) Filed: Dec. 30, 2021

(65) Prior Publication Data
US 2022/0117861 A1 Apr. 21, 2022

Related U.S. Application Data

(63) Continuation of application No. 16/010,082, filed on Jun. 15, 2018, now Pat. No. 11,273,105.
(Continued)

(51) Int. Cl.
| | | |
|---|---|---|
| *A61K 36/00* | (2006.01) |
| *A61K 8/06* | (2006.01) |
| *A61K 9/14* | (2006.01) |
| *A61K 9/107* | (2006.01) |
| *A61K 36/185* | (2006.01) |
| *A61K 8/92* | (2006.01) |
| *A61Q 1/00* | (2006.01) |
| *A61K 36/73* | (2006.01) |
| *B01F 23/411* | (2022.01) |
| *C09K 23/00* | (2022.01) |
| *C09K 23/14* | (2022.01) |
| *C09K 23/16* | (2022.01) |
| *A23L 33/105* | (2016.01) |
| *A61K 8/9789* | (2017.01) |
| *A23L 2/52* | (2006.01) |
| *A61K 8/31* | (2006.01) |
| *A61K 8/34* | (2006.01) |
| *A61K 8/49* | (2006.01) |
| *A61K 31/01* | (2006.01) |
| *A61K 31/05* | (2006.01) |
| *A61K 31/352* | (2006.01) |
| *A61K 36/53* | (2006.01) |
| *A61K 36/534* | (2006.01) |
| *A61K 36/06* | (2006.01) |
| *A61Q 19/00* | (2006.01) |
| *B01F 23/41* | (2022.01) |
| *B01F 101/06* | (2022.01) |
| *B01F 101/14* | (2022.01) |

(Continued)

(52) U.S. Cl.
CPC ............ *A61K 8/068* (2013.01); *A23L 2/52* (2013.01); *A23L 33/105* (2016.08); *A61K 8/062* (2013.01); *A61K 8/31* (2013.01); *A61K 8/347* (2013.01); *A61K 8/498* (2013.01); *A61K 8/922* (2013.01); *A61K 8/9789* (2017.08); *A61K 9/107* (2013.01); *A61K 9/1075* (2013.01); *A61K 9/145* (2013.01); *A61K 31/01* (2013.01); *A61K 31/05* (2013.01); *A61K 31/352* (2013.01); *A61K 36/06* (2013.01); *A61K 36/185* (2013.01); *A61K 36/53* (2013.01); *A61K 36/534* (2013.01); *A61K 36/73* (2013.01); *A61Q 1/00* (2013.01); *A61Q 19/00* (2013.01); *B01F 23/411* (2022.01); *C09K 23/00* (2022.01); *C09K 23/018* (2022.01); *C09K 23/14* (2022.01); *C09K 23/16* (2022.01); *A23V 2002/00* (2013.01); *A61K 2800/10* (2013.01); *A61K 2800/80* (2013.01); *B01F 23/4143* (2022.01); *B01F 23/4145* (2022.01); *B01F 2101/06* (2022.01); *B01F 2101/14* (2022.01); *B01F 2101/21* (2022.01); *B01F 2101/22* (2022.01); *B01F 2101/25* (2022.01)

(58) Field of Classification Search
CPC ..................................................... A61K 8/068
See application file for complete search history.

(56) References Cited

U.S. PATENT DOCUMENTS

| | | |
|---|---|---|
| 4,788,054 A | 11/1988 | Bernhardt et al. |
| 2005/0106304 A1 | 5/2005 | Cook |

(Continued)

FOREIGN PATENT DOCUMENTS

| | | |
|---|---|---|
| CN | 1899051 | 1/2007 |
| CN | 102895186 | 1/2013 |

(Continued)

OTHER PUBLICATIONS

Oomah et al., Characteristics of raspberry (*Rubus idaeus* L.) seed oil. Food Chemistry 69 (2000) 187-193 (Year: 2000).

(Continued)

*Primary Examiner* — Qiuwen Mi
(74) *Attorney, Agent, or Firm* — Krista A. Wittman

(57) ABSTRACT

A method for preparing stable liquid emulsion forms of plant extract is provided. A plant extract having a bitter flavor is mixed with diluent oil as an oil mixture and heat is applied to the oil mixture. An emulsifying agent is dispersed in water as an emulsifying solution. The oil mixture is mixed with the emulsifying solution. The mixed oil mixture and emulsifying solution is homogenized as a liquid form of the plant extract. Gluconic acid is added to the liquid form of the plant extract. The bitter flavor of the plant extract is disguised by adding a bitter blocker to the liquid form of the plant extract.

16 Claims, 2 Drawing Sheets

Related U.S. Application Data

(60) Provisional application No. 62/520,720, filed on Jun. 16, 2017.

(51) Int. Cl.
    *B01F 101/21*     (2022.01)
    *B01F 101/22*     (2022.01)
    *B01F 101/25*     (2022.01)

(56) References Cited

U.S. PATENT DOCUMENTS

| | | |
|---|---|---|
| 2008/0058418 A1 | 3/2008 | D'Angelo et al. |
| 2008/0233060 A1 | 9/2008 | Grune |
| 2010/0323066 A1 | 12/2010 | Comstock |
| 2012/0045489 A1 | 2/2012 | Tong et al. |
| 2013/0150335 A1 | 6/2013 | Liu et al. |
| 2014/0147569 A1 | 5/2014 | Poulsen et al. |
| 2015/0044315 A1 | 2/2015 | Letzel |
| 2016/0143972 A1 | 5/2016 | Stebbins et al. |
| 2016/0361420 A1* | 12/2016 | Junnarkar ............ A61K 9/0024 |
| 2018/0020699 A1 | 1/2018 | Steup |
| 2018/0249747 A1 | 9/2018 | Ma et al. |

FOREIGN PATENT DOCUMENTS

| | | | |
|---|---|---|---|
| CN | 102895186 A | * | 1/2013 |
| JP | 3618030 B2 | * | 2/2005 |
| WO | 99/32107 | | 7/1999 |

OTHER PUBLICATIONS

Sahasrabudhe et al., Density, viscosity, and surface tension of five vegetable oils at elevated temperatures: Measurement and modeling. International Journal of Food Properties 2017, vol. 20, No. S2, S1965-S1981 (Year: 2017).

* cited by examiner

METHOD FOR PREPARING STABLE LIQUID EMULSION FORMS OF PLANT EXTRACT

FIELD

This application relates in general to emulsifying plant extracts, and in particular to a method for preparing stable liquid emulsion forms of plant extract.

BACKGROUND

Oil-based plant components, such as a terpenes, omega-3 oils, lavender, mint oils, tea tree oil, eucalyptus, and cannabinoids, can be used in many different consumer products, such as cosmetics, toiletries, food, and beverages. However, when used in a product, the plant component must be compatible with other ingredients of that product, such as water. Yet, many plant components, once extracted, are oil-based and therefore, hydrophobic. An emulsification step must be performed to ensure the plant component can be combined with the other ingredients.

Further complicating the use of particular plant components in consumer products is that some components are highly viscous, making conventional processes for emulsification unsuitable and ineffective. Thus, prior to performing an emulsification to disperse and stabilize the plant component to become compatible with other product ingredients, the highly viscous plant component must be transformed to a lower viscosity.

Conventional processes for lowering the viscosity include mixing the highly viscous plant component with a diluent, typically a solvent, such as propylene glycol or ethanol, prior to performing the emulsification. A common diluent is alcohol, which dissolves an oil-based hydrophobic plant component, resulting in a lower viscosity mixture of plant component and diluent. An emulsifying step is then performed by combining the alcohol-plant component mixture with water and an emulsifier to disperse the hydrophobic plant component in water. Once completed, the alcohol is removed from the resulting mixture. For example, U.S. Patent Application Publication No. 2016/0143972, to Stebbins, covers a method for preparing a solid form of a cannabinoid by dissolving the cannabinoid in ethanol and later removing the ethanol by performing evaporating and drying steps.

Unfortunately, complete removal of the alcohol is extremely costly, time consuming, and difficult, often leaving residual amounts remaining, as well as removing parts of specific plant components that should remain in the final product. The presence of alcohol, even residual amounts, can impede the stability of the resulting emulsion. Further, the presence of alcohol inhibits stability of a final product, has a shorter shelf life, and can be prohibited by law in some plant extracts, such as from cannabis.

Therefore, there is a need for an approach to convert plant components to a different form for use in consumer products without the use of alcohol or other solvents. Preferably, the conversion process includes an emulsification of large amounts of plant components at a single time to reduce time and cost.

SUMMARY

To utilize plant extract in certain foods, drinks, cosmetics, toiletries, or medicines, the plant extract should be compatible with the other ingredients. However, oil-based plant extracts, such as mint oils, eucalyptus and cannabinoids, are immiscible with water, which makes use of such plant extracts in consumer goods difficult. An emulsification of the plant extract in water can be performed to evenly distribute oil droplets of the plant extract throughout the water for use in such goods. During the emulsification, an emulsifier enrobes the oil droplets of the plant extract within the water. The emulsifier can be a soluble dietary fiber, which can survive the digestive process and are water soluble. Specifically, when enrobed with the soluble dietary fiber emulsifier, the oil droplet passes directly into the intestinal track and is absorbed. Passing the stomach and directly entering the intestinal track reduces an amount of time in which any effects of the plant extract commence, as well as disguises a bitter taste of the plant extract.

An embodiment provides a method for preparing stable liquid emulsion forms of plant extract. A plant extract having a bitter flavor is mixed with diluent oil as an oil mixture and heat is applied to the oil mixture. An emulsifying agent is dispersed in water as an emulsifying solution. The oil mixture is mixed with the emulsifying solution. The mixed oil mixture and emulsifying solution is homogenized as a liquid form of the plant extract. Gluconic acid is added to the liquid form of the plant extract. The bitter flavor of the plant extract is disguised by adding a bitter blocker to the liquid form of the plant extract.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, including time and clustering of events, all without departing from their spirit and the scope. Accordingly, the drawings and detailed description are to be regarded as illustrative in nature and not as restrictive.

DETAILED DESCRIPTION

Conventional processes for emulsification of highly viscous plant extracts include the use of alcohol and other solvents to reduce the viscosity of the plant extract, which can be costly and time consuming. Further, removal of the alcohol is difficult and often, residual amounts of the alcohol remain despite removal, which can impede emulsification stability and create hazardous conditions, such as combustion and explosion, if high heat is applied. Utilizing a different class of compounds, such as a non-solvent based compound, for lowering the viscosity of plant extract can increase the purity of the resulting plant extract, while reducing the loss of higher vapor pressure or more volatile plant components, which are typically removed when alcohol is used as a co-solvent. Additionally, performing an emulsification without alcohol also leads to reduced cost, time spent, and enhanced emulsion stability.

Highly viscous plant components can be converted to a liquid emulsion using non-solvent based compounds for use in beverages, food, and tinctures, as well as other products.

Figure 1:
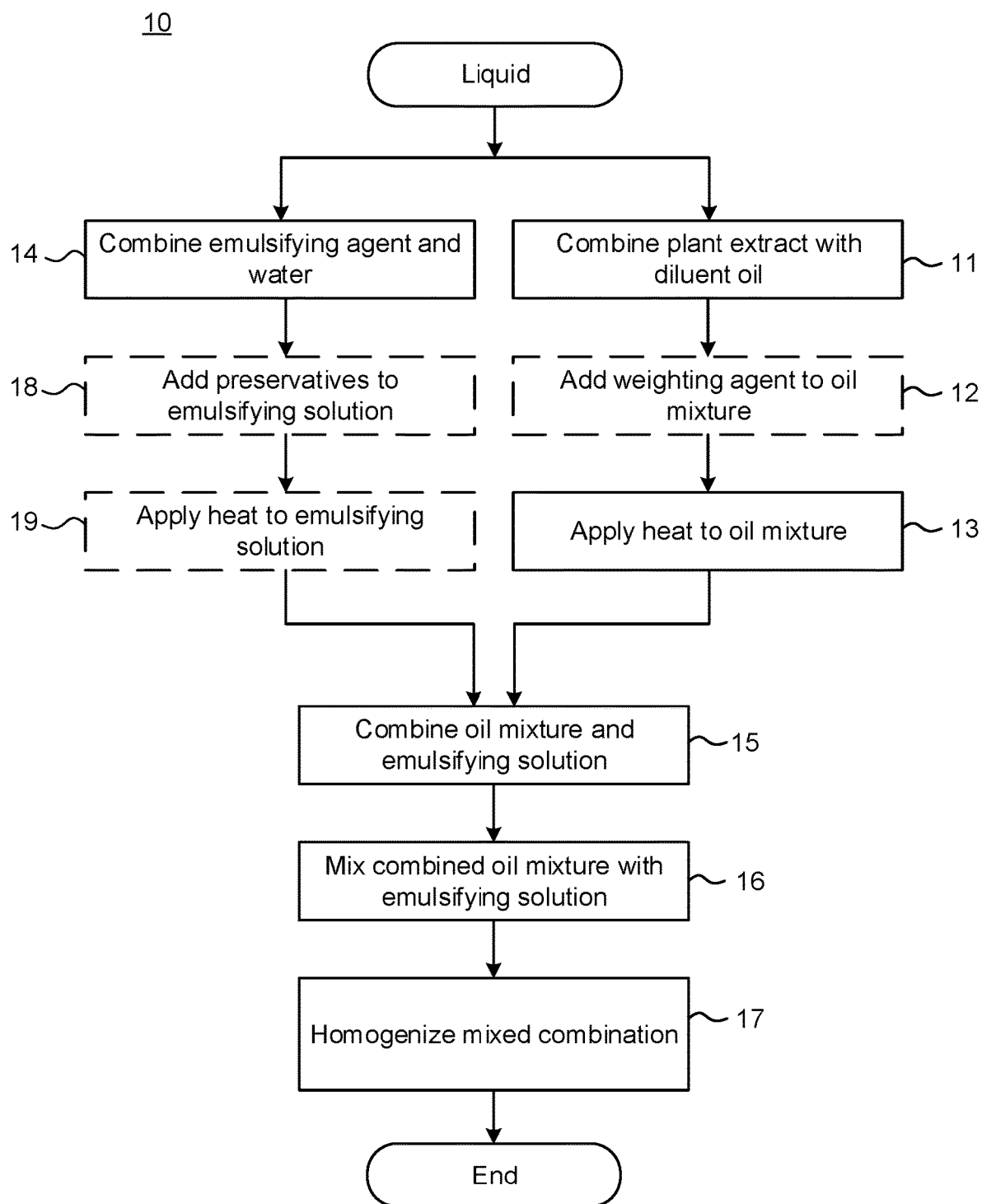
FIG. 1 is a flow diagram showing a method for preparing stable liquid emulsion forms of plant extract, in accordance with one embodiment.

FIG. 1 is a flow diagram showing a method for preparing stable liquid emulsion forms of plant extract, in accordance with one embodiment. Plant extract to be converted to a different form can be obtained in a highly viscous, oil form and combined with a diluent oil (block 11) and optionally, an oil based weighting agent (block 12), as an oil mixture. The plant extract can include one or more components of the plant. A desired plant component can be separated from the other components for emulsification. Alternatively, the different plant components can be emulsified together. The plant extract can have a purity of up to 99.9% and can include one or more of terpenes, omega-3 oils, lavender, mint oils, such as spearmint peppermint, tea tree oil, eucalyptus, and cannabinoids, such as Cannabigerolic acid, Δ9-tetrahydrocannabinolic acid (THCA), Cannabidiolic acid, Cannabichromenenic acid, Cannabigerovarinic acid, Tetrahydrocanabivarinic acid, Cannabidivarinic acid, Cannabichromevarinic acid, Cannabigerol, all forms of Tetrahydrocannabinol (THC), including Δ9-tetrahydrocannabinol and Δ8-tetrahydrocannabinol, Cannabidiol, Cannabichromene, Cannabigerivarin, Tetrahydrocannabivarin, Cannabidivarin, Cannabichromevarin, Cannabinol, and other cannabinoids. In one embodiment, the purity of the plant extract is between 70% and 99%.

The diluent oil should have a lower viscosity than the plant extract and can be selected based on a viscosity of the plant extract. Examples of the diluent oil can include food grade oils, such as vegetable oil, olive oil, canola oil, safflower oil, and rapeseed oil, as well as other types of oils, including mid-chain triglycerides. The diluent oil can include a single type of oil or a blend of different oil types. In one embodiment, the oil mixture can include around 0-90% diluent oil and 10-90% extracted plant oil. In a further embodiment, the diluent oil may not be necessary, such as when the plant extract has an acceptable viscosity of less than around 35,000 cps. For example, when extracting oils from a cannabis plant, THC is extracted with terpenes, which have a low viscosity. Thus, if the THC and terpenes are emulsified together, diluent oil is not necessary since the terpenes lower the viscosity of the THC. In contrast, if THC is separated from the terpenes for emulsification, diluent oil must be added to lower the viscosity of the THC.

A weighting agent has a specific gravity of weight greater than 1.0. The weighting agent can include ester gum, brominated vegetable oil, sucrose acetate isobutyrate or other types of weighting agents, and can increase the density of the plant extract and diluent oil to prevent the oil mixture from floating to the top when combined with water in a later step, which is described further below. In one embodiment, the amount of the weighting agent should be selected based on the desired target density of the resulting oil mixture or based on the extracted plant extract oil. Specifically, the weighting agent should increase the density of oils in the plant extract, which are often less than a specific gravity of 1.0. In one embodiment, the density of the plant extract oils should be raised to a similar density of water. Heat can be applied (block 13) to the oil mixture to enhance mixing of the plant extract and diluent oil, and weighting agent if added. Once the oil mixture reaches a viscosity level of less than around 35,000 cps, the mixture can be combined (block 15) with an emulsifying solution, which can be prepared (block 14) simultaneously with the heating of the oil mixture or at a different time. To prepare (block 14) the emulsifying solution, an emulsifying agent, or emulsifier, is dispersed in water, which acts as a carrier to the plant extract when combined. The emulsifying agent can have low or high hydrophilic-lipophilic balance levels, and can include both water and oil soluble emulsifiers, such as modified food starch, an extract of the *Quillaja saponaria Molina* tree, known as Q-Naturale, lecithin, monoglycerides, gum acacia, diglycerides, sucrose monopalmitate (P90), polysorbate 80 (tween 80), or polysorbate 20 (tween 20), as well as various proteins. Other emulsifying agents are possible.

Concentration of the emulsifying agent is first determined by its nature based on an emulsifying strength and then as a function of the oil mixture to be added. Different emulsifying agents can be used at a different ratio of emulsifier to oil mixture. For example, the emulsifying agents, Gum Acacia and modified food starch, can be used at a ratio of 1 part oil mixture to 0.1 to 4.0 parts emulsifying agent. Meanwhile, mono and/or diglycerides, Tween 20 or 80, and Q-Natural could be used at lower levels ranging from 1 part oil mixture to 0.1 to 1.0 emulsifying agent.

In one embodiment, preservatives can be added (block 18) to the emulsifying solution to increase shelf life of the resulting emulsion. Examples of components that can be used as a preservative include, but are not limited to, one or more of potassium sorbate, sodium benzoate, ascorbic acid, gluconic acid, and citric acid. The preservatives can also be added at other steps, such as to the oil mixture or to the combined oil mixture and emulsifying solution.

In one embodiment, heat can be optionally applied (block 19) to the emulsifying solution and preservatives to assist in reduction of the viscosity of the emulsifying solution. Reducing the viscosity can lead to the use of less diluent oil in the oil mixture.

Once the oil mixture and the emulsifying solution are combined (block 15), the emulsifying agent surrounds the oil droplets of the oil mixture or the plant extract itself to stabilize the resulting emulsion. The combination is placed in a mixer, such as a high or low shear mixer, to undergo (block 16) shearing to reduce a particle size of the emulsified oil mixture or plant extract, if no diluent oil is used. The mixer can be a Silverson or IKA high shear mixer, however, other mixers are possible. At a minimum, the mixer should be able to produce a minimum of 3,000 rpms and above. Mixing should continue until oil droplets formed from the oil mixture or plant extract have a particle size less than 5 to 10 microns. In one embodiment, the oil droplets are less than 2 microns.

After removal from the mixer, the combination can be homogenized (block 17) mechanically using a high pressure mechanical homogenizer, such as by APV or GEA Niro, or sonically using a high energy ultrasonic device, such as the Biosonics Ultrasonic homogenizer, to further reduce a size of the oil droplets. Homogenization of the combination can enhance long term stability by reducing particle size, which reduces the rate at which the resulting emulsion will separate, thereby, enhancing shelf life stability. Performance of the manual homogenization can be optional based on a desired shelf stability of the liquid form of the plant component. For example, if only a short shelf life is required for a product, there may be no need to perform manual homogenization.

After homogenization of the combination, the oil droplets can be reduced to a size less than 1 micron. In one embodiment, the oil droplet size is less than 0.5 microns. Performing the emulsification and then homogenization enables large volumes of the oil-based plant extract to be processed in a reduced amount of time, in contrast to ultrasonic homogenization, which is inappropriate for large scale manufacture.

Further, a multiple step process allows for different sized particles after each step, which can be used in different types of consumer products. For example, coarser particles can be used as a clouding agent for beverages, while finer particles can be used in clear beverages.

The resulting liquid combination is stable, and thus non-separating, at room temperatures for periods of time up to six months or perhaps, longer. The smaller the emulsified particles and/or the more closely the densities of the emulsified oil droplets match the water phase, the more stable the emulsion becomes since the smaller size particles results in lower mass and thus, the gravitational forces driving separation of the plant extract are reduced. Further, the smaller the emulsified particle, the clearer the resulting emulsion becomes, which can be an important attribute, especially for food products, such as beverages.

Particle size of the emulsified oil and nature of the emulsifier also play a role in the ingestion and metabolic rates of the plant extract being later consumed. For instance, some emulsifiers are soluble dietary fibers, which are characterized as mucilage that can survive the digestive process and are water soluble. As a result, if the dietary fiber is water soluble, the mucilage can be absorbed in the digestive track. Specifically, the mucilage and oil droplets directly enter the blood stream by bypassing the liver and are absorbed faster, reducing the time of the desired plant extract, such as cannabinoids, to take effect. In one embodiment, the time is shortened to 10 to 20 minutes for digestion of the resulting emulsion, in contrast to one to three hours for a traditional edible food or drink product with cannabis.

Further, the resulting emulsion can isolate and disguise a bitterness of a particular plant extract. Specifically, the emulsifying agent, or emulsifier, can be selected based in part on that emulsifier's native, neutral taste. The emulsifier enrobes the bitter tasting oil droplet and as a soluble dietary fiber, the enrobed oil droplet is not digested in the stomach and passes directly into the intestinal track and absorbed, thus avoiding the bitter taste. The bitterness can also be disguised using bitter blockers. For example, with respect to cannabis, the plant extract may include THC and terpenes, which generally have a bitter taste. The bitterness of the terpenes can be disguised with bitter blockers, such as sugar, non-nutritive sweeteners, such as stevia or sucralose, and various flavonoids, to generate a sweet taste. In a further embodiment, terpenes can also be used as a bitter blocker.

The resulting emulsion can be combined with flavor, sugars, colorants, or other liquids, such as water and juice for sale as a beverage, or used as a cooking or baking ingredient for food, including in dry mixes, meal replacements, baked goods, and raw foods. Additionally, the emulsified liquid can be used in other non-food products, such as cosmetics, toiletries, and medical products, such as saline solution, cough syrup, sexual lubricants, and inhalers. The resulting liquid can also be used in many other products. For example, the resulting liquid can be utilized in frozen items, such as food, medicine or other goods, without separating due to the stability of the resulting liquid. Additionally, when used in food, the oil droplets are uniformly dispersed throughout the food so that one portion of a food item does not include high amounts of the plant extract, while other portions include very little.

Figure 2:
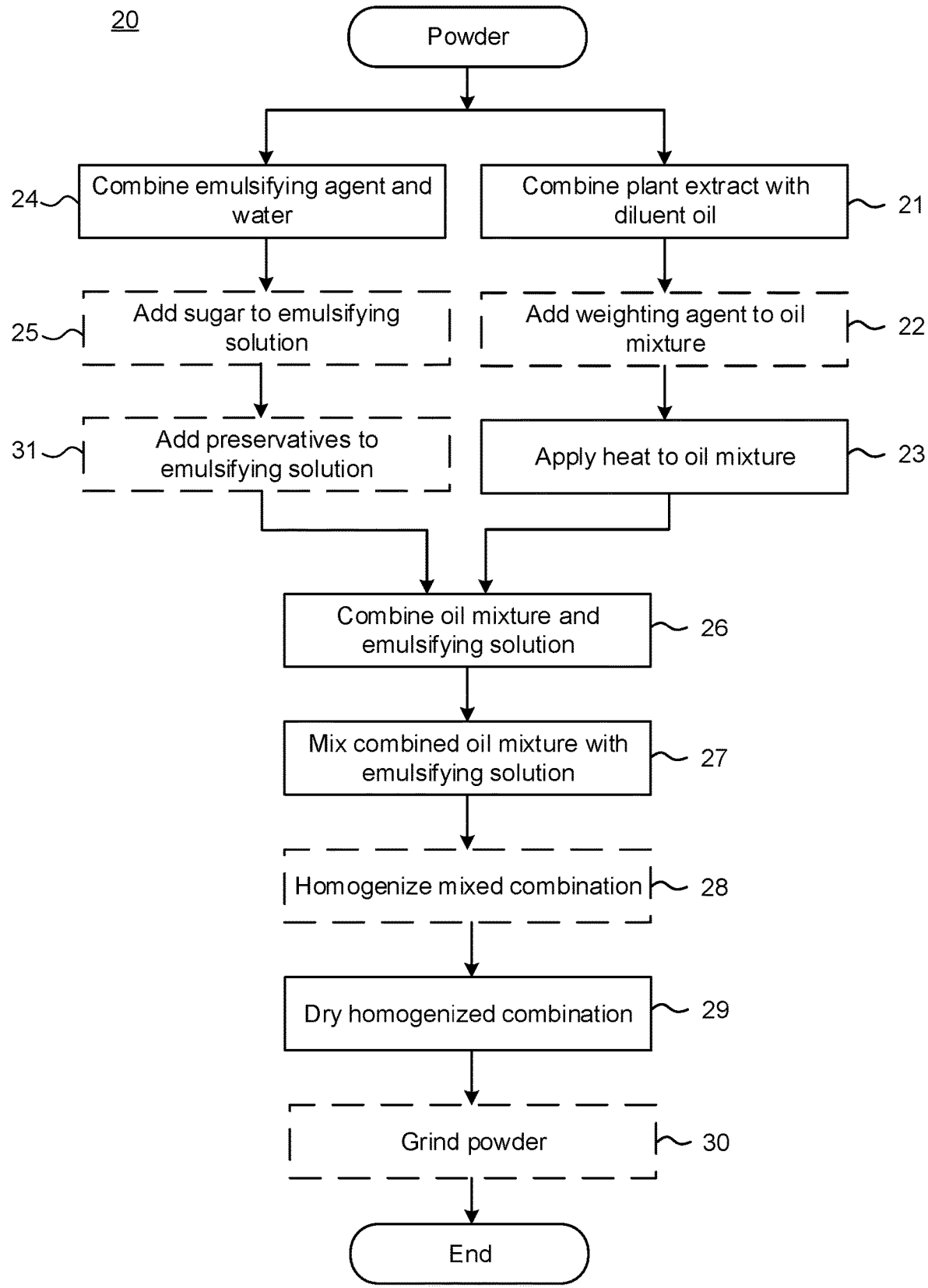
FIG. 2 is a flow diagram showing a method for preparing stable powder emulsion forms of plant extract, in accordance with one embodiment.

In addition to liquid form, the plant extract can also be converted to a powder form. FIG. 2 is a flow diagram showing a method for preparing stable powder emulsion forms of plant extract, in accordance with one embodiment. Plant extract, including one or more of terpenes, omega-3 oils, lavender, peppermint, tea tree oil, eucalyptus, and cannabinoids, such as Cannabigerolic acid, $\Delta$9-tetrahydrocannabinolic acid, Cannabidiolic acid, Cannabichromenenic acid, Cannabigerovarinic acid, Tetrahydrocanabivarinic acid, Cannabidivarinic acid, Cannabichromevarinic acid, Cannabigerol, all forms of THC, including, $\Delta$9-tetrahydrocannabinol and $\Delta$8-tetrahydrocannabinol, Cannabidiol, Cannabichromene, Cannabigerivarin, Tetrahydrocannabivarin, Cannabidivarin, Cannabichromevarin, Cannabinol, and other cannabinoids, is obtained in a highly viscous form. The viscosity of the plant extract is lowered to around less than 35,000 cps by combining (block 21) the plant extract with a lower viscosity diluent oil, such as vegetable oil or other types of oils, to form an oil mixture. In one embodiment, the diluent oil is selected based on the plant extract to ensure the diluent oil has a lower viscosity than the plant extract. However, if the plant extract already has a lowered viscosity, no diluent oil is necessary and the plant extract can be combined with the weighting agent.

Optionally, a weighting agent, such as ester gum, brominated vegetable oil, sucrose acetate isobutyrate, or other weighting agents can be added (block 22) to the oil mixture or plant extract to balance or match the density of the oil mixture with that of the water phase. Subsequently, heat can be applied (block 23) to the oil mixture and weighting agent, if any, to enhance mixing of the plant extract and diluent oil.

Simultaneously or at a different time, an emulsifying agent, such as gum acacia, modified food starch, Q-Naturale, lecithin, monoglycerides, diglycerides, tween 80, or tween 20 is dispersed (block 24) in water to create an emulsifying solution. Optionally, a sugar, such as a corn syrup solid or maltodextrin, or other food grade plating agent, such as starch, modified starch or a carbohydrate, including gum acacia, can be added (block 25) as a carrier for the oil, to the emulsifying solution, to increase an efficiency of drying performed subsequent to an emulsification of the oil mixture and emulsifying solution, as further described below. In a further embodiment, preservatives can be added (block 31) to the emulsifying solution to increase the shelf life of the combination resulting from the emulsion.

Once the oil mixture is heated and a viscosity of the mixture is less than 35,000 cps, the oil mixture is combined (block 26) with the emulsifying agent for performing the emulsification. The combination of the oil mixture and emulsifying agent is placed in a high shear mixer for shearing (block 27), which occurs based on a high speed of rotation. In one embodiment, the mixing speed should be 1,000 rpms or greater. Mixing should until a size of the oil droplets of the plant extract, in the combination, can measure less than 50 microns.

Next, the combination can be optionally homogenized (block 28) mechanically or sonically, using homogenizers, as described above with respect to FIG. 1 to obtain smaller size emulsified particles. However, in one embodiment, if the particle sizes are less than 5 to 10 microns, no homogenization may be necessary. The droplets of the oil mixture or plant extract, in the combination, resulting after homogenization can measure below 1 micron. However, regardless of whether homogenization occurs, the resulting combination can be de-watered or dried (block 29) using a spray dryer, such as GEA Niro, Buchi, or APV, a drum drier, or on a sheet in an oven. Finally, the dried combination can be optionally ground (block 30) to a desired particle size. In one embodiment, the particle size can be selected based on the product into which the ground plant extract will be used.

In one example, a powered form of the plant extract can be packaged as a beverage mixer for putting in a water bottle to add the plant component. Other examples include use as a seasoning for placing in foods, for mixing in cosmetics, and to be compressed into a pill.

In one embodiment, the plant extract can include a cannabinoid or a combination of cannabinoids, such as Tetrahydrocannabinol and Cannabidiol, as well as other types of cannabinoids. The cannabinoids can start in a high viscous form, such as a powder and can be converted to a liquid or a different form of the powder for dissolution in water. Use of the optional weighting agent can prevent oil droplets in the liquid form or in the dissolved power form, such as reconstituted from water, from rising to the top of the liquid or dissolution and helps to evenly distribute the oil droplets to stabilize the converted liquid form of the cannabinoid.

While the invention has been particularly shown and described as referenced to the embodiments thereof, those skilled in the art will understand that the foregoing and other changes in form and detail may be made therein without departing from the spirit and scope of the invention.

What is claimed is:

1. A method for preparing stable liquid emulsion forms of plant extract, comprising:
    mixing a plant extract for eating or drinking by an individual and comprising a bitter flavor with diluent oil as an oil mixture;
    applying heat to the oil mixture;
    dispersing an emulsifying agent in water as an emulsifying solution;
    mixing the oil mixture and emulsifying solution;
    homogenizing the mixed oil mixture and emulsifying solution as a liquid form of the plant extract;
    adding gluconic acid to the liquid form of the plant extract; and
    disguising the bitter flavor of the plant extract by adding a bitter blocker to the liquid form of the plant extract, wherein the liquid form of the plant extract with the bitter blocker is ingested by the individual.

2. A method according to claim 1, wherein the plant extract comprises one of terpenes, omega-3 oils, lavender, mint oils, tea tree oil, eucalyptus, and cannabinoids comprising one or more of Cannabigerolic acid, Δ9-tetrahydrocannabinolic acid, Cannabidiolic acid, Cannabichromenenic acid, Cannabigerovarinic acid, Tetrahydrocanabivarinic acid, Cannabidivarinic acid, Cannabichromevarinic acid, Cannabigerol, Tetrahydrocannabinol, Δ9-tetrahydrocannabinol, Δ8-tetrahydrocannabinol, Cannabidiol, Cannabichromene, Cannabigerivarin, Tetrahydrocannabivarin, Cannabidivarin, Cannabichromevarin, and Cannabinol.

3. A method according to claim 1, wherein a purity of the plant extract comprises 70% to 99% of the oil mixture.

4. A method according to claim 1, wherein the diluent oil comprises one of vegetable oil, olive oil, canola oil, safflower oil, rapeseed oil, and mid-chain triglycerides.

5. A method according to claim 1, wherein the diluent oil has a lower viscosity than the plant extract.

6. A method according to claim 1, further comprising:
    adding a weighting agent to the oil mixture.

7. A method according to claim 6, wherein the weighting agent comprises one or more of ester gum, brominated vegetable oil, and sucrose acetate isobutyrate.

8. A method according to claim 1, wherein the emulsifying agent comprises one or more of modified food starch, an extract of *Quillaja Saponaria Molina* Trees, lecithin, monoglycerides, gum acacia, diglycerides, sucrose monopalmitate, polysorbate 80, polysorbate 20, and protein.

9. A method according to claim 1, wherein a concentration of the emulsifying agent comprises a ratio of one part of the oil mixture to four parts or less of the emulsifying agent.

10. A method according to claim 1, comprising:
    adding a preservative to the emulsifying solution.

11. A method according to claim 10, wherein the preservative comprises one or more of potassium sorbate, sodium benzoate, ascorbic acid, and citric acid.

12. A method according to claim 1, further comprising:
    applying heat to the emulsifying agent prior to mixing with the oil mixture.

13. A method according to claim 1, further comprising:
    mixing the oil mixture and the emulsifying solution using one of high and low shear mixers.

14. A method according to claim 1, further comprising:
    adding the liquid form of the plant extract to one or more of a liquid, saline solution, food, cough syrup, and frozen food, pills, tablets, and dry food mixes.

15. A method according to claim 1, wherein droplets of the plant extract comprise a size less than 2 microns.

16. A method according to claim 1, wherein the liquid form of the plant extract comprises a shelf life of around six months.

* * * * *